United States Patent
Lennon et al.

(10) Patent No.: US 6,486,347 B2
(45) Date of Patent: Nov. 26, 2002

(54) PREPARATION OF PHOSPHINE LIGANDS

(75) Inventors: Ian Campbell Lennon, Cambridge (GB); Ulrich Berens, Cambridge (GB)

(73) Assignee: Chirotech Technology, Ltd. (GB)

( * ) Notice: Subject to any disclaimer, the term of this patent is extended or adjusted under 35 U.S.C. 154(b) by 0 days.

(21) Appl. No.: 09/821,446

(22) Filed: Mar. 29, 2001

(65) Prior Publication Data

US 2001/0011145 A1 Aug. 2, 2001

Related U.S. Application Data

(63) Continuation of application No. 09/285,587, filed on Apr. 2, 1999, now abandoned.
(60) Provisional application No. 60/087,444, filed on Jun. 1, 1998.

(30) Foreign Application Priority Data

Apr. 2, 1998 (GB) ............................................. 9807104

(51) Int. Cl.$^7$ ........................... C07F 9/28; C07C 231/02
(52) U.S. Cl. ........................... 564/15; 564/139; 564/155
(58) Field of Search ........................ 562/405; 585/531; 564/139, 155, 15

(56) References Cited

U.S. PATENT DOCUMENTS

| | | |
|---|---|---|
| 3,758,558 A | 9/1973 | Mason et al. |
| 5,399,771 A | 3/1995 | Cai et al. |
| 5,739,396 A | 4/1998 | Trost et al. |
| 5,756,804 A | 5/1998 | Haber et al. |
| 5,801,263 A | 9/1998 | Seitz et al. |

FOREIGN PATENT DOCUMENTS

| DE | 2264088 | 7/1973 |
|---|---|---|
| WO | 9312260 | 6/1993 |

OTHER PUBLICATIONS

Hingst, Martin, Michael Tepper, Othmar Stelzer (1998) "Nucleophilic Phosphanylation of Fluoroaromatic Compounds with Carboxyl, Carboxymethyl, and Aminomethyl Functionalities—an Efficient Synthetic Route to Amphiphilic Arylphosphanes" *Eur. J. Inorg. Chem.* pp. 73–82.

Hoots, John E., Thomas B. Rauchfuss, Debra A. Wrobleski (1982) *Inorg Synthese* (21):175–179.

Coote, Seven J., Graham J. Dawson, Christopher G. Frost, Jonathan M. J. Williams (Jul. 1993) "The Preparation of Functionalised Aryl Phosphines from Aryl Fluorides by Nucleophilic Aromatic Substitution with Potassium Diphenylphosphide" *Synlett* pp. 509/.

*Primary Examiner*—Shailendra Kumar
(74) *Attorney, Agent, or Firm*—Saliwanchik, Lloyd & Saliwanchik

(57) ABSTRACT

A process for the preparation of a compound having the formula $$R^3R^4P{-}Ar{-}CO{-}X$$

wherein Ar is an aryl group bearing the $PR^3R^4$ and COX groups in a 1,2-relationship, and optionally bearing also one or more non-interfering groups, $R^3$ and $R^4$ are each a hydrocarbon group optionally substituted by any non-interfering group, and X is OH or a non-interfering group, comprises (i) the reaction of $NaPR^3R^4$ with F—Ar—COX, or (ii) when X is an amine group, the reaction of $R^3R^4P$—Ar—COOY, OY being OH or a leaving group, with a solution of the amine obtained in situ by adding a base to a salt thereof.

Certain ligands prepared by such a process are in a novel, crystalline form.

14 Claims, No Drawings

PREPARATION OF PHOSPHINE LIGANDS

This application is a continuation of 09/285,587, filed Apr. 2, 1999, now abandoned, and also claims benefit of 60/087,444, filed Jun. 1, 1998.

FIELD OF THE INVENTION

This invention relates to processes suitable for the large-scale preparation of enantiomerically-enriched phosphines, especially those useful as ligands in asymmetric allylic substitution catalysts.

BACKGROUND OF THE INVENTION

Chiral phosphine ligands such as (1) and (2), and the opposite enantiomers thereon have been shown to be effective in palladium(O)-catalysed asymmetric allylic substitution reactions. For a review, see B. M. Trost and D. L. Van Vranken, *Chem Rev.* (1996) 96:395. For specific examples of such ligands, see WO-A-93 12260, B. M. Trost and X. Ariza, *Angew. Chem. Int. Ed. Engl.* (1997) 36:2635, and B. M. Trost and F. D. Toste, *J. Am. Chem. Soc.* (1998) 120:815.

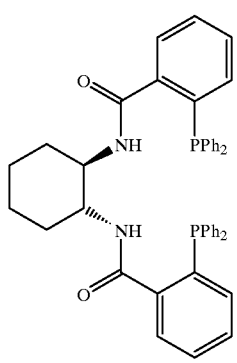

(1)

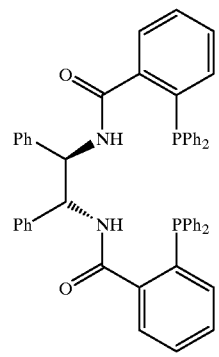

(2)

CAS [138517-62-1]

Such catalysts are eminently suitable for industrial applications, especially for the provision of chiral pharmaceutical intermediates in high enantiomeric purity. For this purpose, and in other industrial applications such as flavour and fragrance fine chemicals, the development of manufacturing processes requires in turn large amounts of a ligand such as (1) or (2), e.g. in kilogram quantity or greater. Thus, there is a requirement for efficient and scaleable methods for synthesis of such ligands.

A process for the manufacture of these ligands has been described by B. M. Trost. D. L. Van Vranken and C. Bingel, *J. Am. Chem. Soc.* (1992) 114:9327. This process is depicted in Scheme 1.

Scheme 1

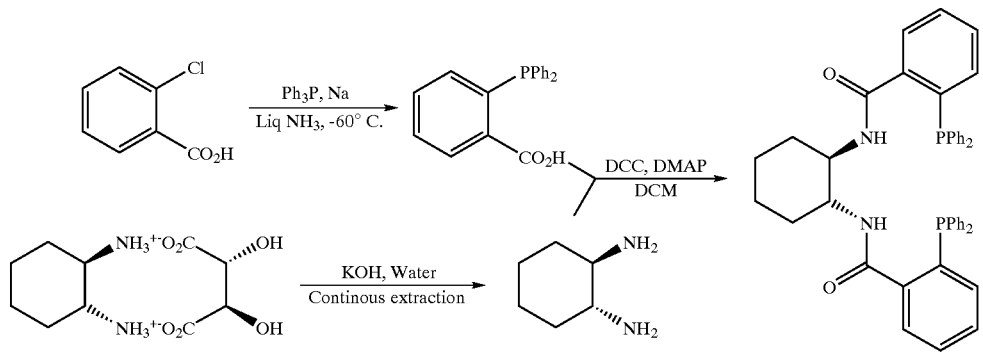

There are several limitations to using the methods described for the manufacture of this class of ligands on a commercially useful scale.

Firstly, the conversion of 2-chlorobenzoic acid to 2-(diphenylphosphino)benzoic acid gives modest yields, using literature methods. A 74% yield for this process is reported in DE-A-2264088, but in our hands this process gave yields in the range of 48 to 54% on a 1 to 2 kg scale. Typically, yields in the range of 40 to 50% are obtained; see *Inorg Synth.* (1982), 21:175, where a 49% yield is quoted.

An alternative method for preparing this class of phosphines has been described, starting from a fluoro-derivative; see Williams et al, *Synlett.* (1993) 509. An example is as follows:

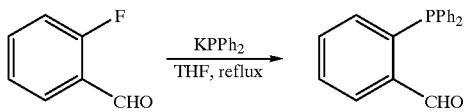

This paper specifically states that 2-fluorobenzoic acid and the corresponding carboxylate did not provide the desired product under these conditions.

Hingst et al, Eur. J Inorg. Chem. (1998) 73, reports that the nucleophilic phosphanylation of 2-fluorobenzoic acid with Ph$_2$PH in superbasic medium gave poor yields, and that a "fair yield" is obtained if a solution of Ph$_2$PK in THF is used to phosphanylate the K salt of 2-fluorobenzoic acid.

Secondly, the diamine has to be isolated from its salt. The tartrate salt is commonly used to provide enantiomerically-pure diamine; see E. N. Jacobsen et al, *J. Org. Chem.* (1994) 59:1939, and references therein, for 1,2-diaminocyclohexane, and E. J. Corey and S. Pikul, *Org Synth.* (1992) 71:22, for 1,2-diphenyl-1,2-ethylenediamine. This salt has to be cracked, and then the air-sensitive and water-soluble diamine has to be extracted from aqueous solution. U.S. Pat. No. 5,399,771 describes an alternative method, where the tartrate salt is slurried in methanolic KOH, potassium tartrate is removed by filtration, and the diamine is isolated after evaporation of the solvent. This method still requires isolation of the sensitive diamine.

Thirdly, coupling of the diamine with 2-diphenylphosphino)benzoic acid using 1,3-dicyclohexylcarbodiimide (DCC) gives the desired product in yields ranging from 60 to 90%, but requires silica chromatography for purification. The ligand is isolated as a waxy or glassy solid, with a broad melting point range 80–120° C.; see Trost et al (1992) supra.

The known synthesis of the desired ligands is suitable for the preparation of 10 to 100 g samples, but is not economic for kilogram quantities of ligands. The poor yield of 2-(diphenylphosphino)benzoic acid is one factor that directly impacts on the commercial viability of the process. Isolation of the diamine, chromatography of the ligand, and the non-crystalline nature of the ligand isolated, all make the current process inefficient.

U.S. Pat. No. 5,801,263 discloses the following reaction

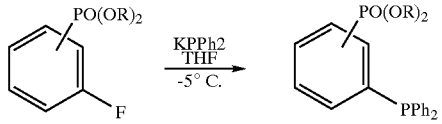

SUMMARY OF THE INVENTION

The present invention is based on three discoveries that give rise to an efficient, scaleable and economical synthesis of compounds effective as ligands, especially those represented by formula (3)

(3)

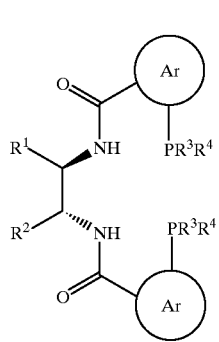

and the opposite enantiomers thereof, wherein Ar is an aromatic ring bearing the PR$^3$R$^4$ and CO groups in a 1,2-relationship. Ar is also optionally substituted by one or more non-interfering groups. The respective R groups are each any non-interfering group, or R$^1$ and R$^2$ may be joined to form a ring.

One aspect of the invention concerns the use of 2-fluorobenzoic acid in the reaction with NaPPh$_2$, e.g. generated from triphenylphosphine, sodium and liquid ammonia at −60° C., to provide 2-(diphenylphosphino) benzoic acid. Analysis of the crude product from the reaction of NaPPh$_2$ with 2-chlorobenzoic acid showed that the major by-product was 3-(diphenylphosphino)benzoic acid, probably arising from benzyne formation and phosphine addition. Thus, several recrystallisations are required to access pure product and lower yields are obtained. Replacing 2-chlorobenzoic acid by the 2-fluoro derivative led to the surprising discovery that yields of 2-(diphenylphosphino) benzoic acid ranging from 75 to 85% could be obtained, with no significant contamination from 3-(diphenylphosphino)benzoic acid. Thus, a key component of the ligand system can be manufactured more efficiently.

A second aspect of this invention concerns the coupling of 2-(diphenylphosphino)benzoic acid, or a derivative thereof represented by formula (4), with a diamine, such as 1,2-diaminocyclohexane, represented by formula (5). An important feature of this invention is that, when the diamine is released from a salt form, such as the tartrate salt represented by formula (6), prior to the coupling reaction, there is no need to isolate the diamine from aqueous solution. Accordingly, the amine is generated in situ, by which is meant that it is not isolated.

(4)

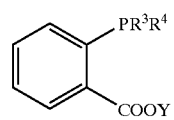

(5)

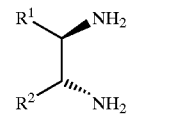

(6)

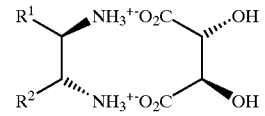

Surprisingly, a mixed anhydride of 2-(diphenylphosphino)benzoic acid with diphenyl chlorophosphate (4: $R^3=R^4=Ph$ and $Y=PO(OPh)_2$) in dichloromethane reacts with an aqueous solution of the diamine (5)/potassium tartrate salt mixture. This mixture is obtained by dissolving the tartrate salt (6) in water and adding potassium carbonate or another, equivalent base. This provides the ligand, e.g. (1), in quantitative crude yield. An unexpected feature is that very little hydrolysis of the mixed anhydride to the acid is observed in this reaction, and excellent conversion to the ligand is obtained.

Another aspect of the present invention is that, surprisingly, the ligand is obtained in a crystalline form, whereas the literature protocol affords ligand as a glassy solid. Thus, the process of the present invention has advantages with respect to material handling and transfer. For example, isolation and purification of the ligand, after the coupling reaction, are simple. The reaction carried out as described above, is very clean and few by-products are seen. No extensive chromatography is required. In particular, after a simple filtration of the crude ligand through silica gel, the ligand can be recrystallised from hot acetonitrile, or acetonitrile/acetone mixtures, to provide the preferred crystalline ligand (1) with a sharp melting point (134–136° C.). The yield of isolated pure, crystalline ligand is between 65 to 75%.

These discoveries allow the ligand to be manufactured on a large scale, with no need for extensive chromatography, and in reproducible quality.

DESCRIPTION OF THE INVENTION

The nature of $R^1$, $R^2$, $R^3$, $R^4$ or any substituent on the Ar rings. e.g. of up to 10, 20 or 30 C atoms, is not critical to the invention. It will be evident to the skilled man, as to which substituents will or will not affect the reaction. Similarly, while Y is preferably —$P(O)(OZ)_2$, and Z is preferably a hydrocarbon substituent, most preferably phenyl, it will be evident that the nature of Y is determined only by the requirement that OY is a leaving group.

Ar represents an aryl (including heteroaryl) ring. It may be monocyclic. Examples of Ar include furan, thiophene and, preferably, benzene rings. The position of the essential substituents on the ring represented by Ar is determined by the requirement that the product acts as a ligand, e.g. that it can act to complex transition metals such as palladium, rhodium, platinum or iridium. Ar is most preferably 1,2-phenylene. Similarly, each of $R^3$ and $R^4$ may be any group that allows the final product to act as a ligand, e.g. methyl or other alkyl group, phenyl or other aryl group, e.g. of up to 10 or 20 C atoms.

The following Examples illustrate the present invention.

EXAMPLE 1

(1R, 2R)-(—)-1,2-Diaminocyclohexane L-Tartrate

Racemic trans-1,2-diaminocyclohexane (625 g, 5.47 mole, 1 Wt) is added to a solution of L-(+)-tartaric acid (821.5 g, 5.47 mole, 1.32 Wt) dissolved in water (3750 ml, 6 vols). This process is exothermic, the internal temperature increases to 60–70° C. After approximately half the amine is added, crystals appear. After complete addition of the amine, the mixture is heated to 100° C. to obtain complete solution.

The mixture is cooled to room temperature, then to 5° C. The solids are filtered and the filter cake washed with 500 ml of ice-cold water, to remove the yellow colour. The cake is washed with methanol (5×300 ml) and then dried in a vacuum oven at 40° C. This affords the tartrate salt (560 g, 80% Th).

If the diastereomeric excess is <98%, then the salt is recrystallised from boiling (100° C.) water (10 vols). Typical recovery 70%, white crystalline material. This also improves the appearance of the product.

Similarly, the use of D-(—)-tartaric acid to resolve racemic amine gives (1S, 2S)-(+)-1,2-diaminocyclohexane D-tartrate.

Enantiomeric excess of diamine component of salt (by chiral HPLC assay on the bis-toluoyl derivative, L-leucine column, 5 µm, 0.5 ml/min, 254 nM, 8% IPA/92% Heptane) >98% ee.

EXAMPLE 2

(1S, 2S)-(+)-1,2-Diaminocyclohexane D-Tartrate

The mother liquors (5750 ml, containing 900 g salt approximately) enriched in (1S, 2S)-(+)- 1,2-diaminocyclohexane L-tartrate are stirred at 20° C. and calcium hydroxide (252 g, 1 eq) is added in portions, pH change from 6.5–10.7. The mixture is stirred for 1 hour at 15–20° C., filtered and the filter cake (calcium tartrate) washed with water (700 ml). The combined filtrates (6650 ml) are heated to 50° C. and D-tartaric acid (562 g, 1.1 eq) added. The mixture is heated to 70° C. and complete solution obtained. After cooling to 5° C., some crystals formed. The crystals are filtered and the filter cake washed with methanol (5×300 ml). The crystals are dried in a vacuum oven at 40° C. to afford the salt as brownish crystals (430 g, 96% Th). The methanolic filtrates are added to the aqueous filtrates and another crop obtained, as a off-white powder (175 g, 38% Th). This material is contaminated with calcium tartrate, and is therefore recrystallised from boiling (100° C.) water (10 vols). Typical recovery 70%, white crystalline material.

Enantiomeric excess of diamine component of salt (by chiral HPLC assay on the bis-toluoyl derivative, L-leucine column, 5 µm, 0.5 ml/min, 254 nM, 8% IPA/92% Heptane): each crop >98% ee.

EXAMPLE 3

2-(Diphenylphosphino)benzoic Acid

Liquid ammonia (approximately 400–500 ml) is condensed into a 3 litre flask, cooled in an acetone/dry ice bath. The reaction flask is fitted with a dry ice condenser, a thermometer, and a pressure equalised dropping funnel. The mineral oil from the sodium spheres is removed by washing with petrol in a filter funnel, the spheres are dried on filter paper and 33.86 g (1.47 mol, 2 eq) added to the ammonia, in 5 g portions, at −60° C. After stirring the mixture for 30 minutes and cooling to −70° C., a solution of triphenylphosphine (193 g, 0.736 mol, 1 eq) in tetrahydrofuran (250 ml) is added over 30 minutes. The internal temperature is maintained between −70° C. to −55° C. The reaction mixture is stirred for 1.5 hours; this gives a blood red solution of sodium diphenylphosphide. Next, a solution of 2-fluorobenzoic acid (100 g, 0.714 mol, 0.97 eq) in tetrahydrofuran (250 ml) is added over 1 hour. The internal temperature varies between −70° C. to −60° C. The mixture is stirred at −60° C. for two hours, then allowed to warm to room temperature over 12 hours. An orange mass is produced. Water (1.5 L) is added carefully and the solid dissolves within 30 minutes. The yellow turbid solution is extracted with methyl tert-butyl ether (300 ml) and the organic extract is discarded. The yellow aqueous phase is acidified with conc. hydrochloric acid (170 ml) to pH 1, this process is exothermic. The acidified aqueous phase is extracted with dichloromethane (2×400 ml). the combined organic phases are washed with water (500 ml ) and brine (500 ml). The clear yellow organic phase is dried (MgSO$_4$), filtered and evaporated under reduced pressure to give a viscous yellow mass, this solidified on standing. The solid is recrystallised from boiling methanol (1.2 Litres) to yield a pale yellow solid. The solid is washed with cold methanol (100 ml) to give 187 g of product, methanol wet (87% Th). This is dried in a vacuum oven at 60° C. Yield: 165.8 g. 77% Th. Mpt=182–184° C.

EXAMPLE 4

(+)-1,2-Bis-N-[2'-(diphenylphosphino)benzoyl]-1 (R), 2(R)-diaminocyclohexane 2-(Diphenylphosphino)benzoic acid (20 g, 65.3 mmol, 2 eq) is suspended in dichloromethane (150 ml) and cooled in an ice/water bath to 0° C. (internal temperature). Triethylamine (10.1 ml, 71.8 mmol) is added dropwise and a clear solution is obtained. This process is exothermic and a rise to 5° C. is observed. The solution is re-cooled to 0° C. and diphenylchlorophosphate (13.4 ml, 64.7 mmol, 1.98 eq) added slowly, maintaining the internal temperature between 0–5° C. The yellow solution is stirred for 1 hour at 0° C. During this time a precipitate is observed (NEt$_3$.HCl).

The (R,R)-1,2-diaminocyclohexane-L-tartrate salt (8.63 g, 32.65 mmol, 1 eq) is suspended in water (50 ml, 5.8 vol) and potassium carbonate (15 g, 107.8 mmol, 3.3 eq, 1.74 wt) added. This process is exothermic and a clear solution is obtained after approximately 10 minutes.

After 30 minutes, the clear aqueous solution of diamine is added to the mixed anhydride at 0° C., and the resulting yellow two-phase mixture is stirred for 2 hours at 0° C., then allowed to warm to room temperature. After 14 hours, the mixture is poured into a 1 litre separating funnel, 200 ml of dichloromethane and 100 ml of water are added. The organic phase is separated, washed with 2 N HCl (100 ml) and saturated NaHCO$_3$ (soln) (100 ml), then dried over magnesium sulphate. The dried organic phase is filtered through a silica pad and the pad is washed with dichloromethane (50 ml). The combined filtrates are evaporated to dryness under reduced pressure, producing a yellow foam (22.3 g, 99% Th crude).

The foam is crystallised from boiling acetonitrile (390 ml, 17.5 vols) to afford a white crystalline solid. The solid is dried under vacuum to provide the title compound ( 15 g, 67% Th).

Mpt=134–136° C.

TLC (35% EtOAc/Hexanes) Rf=0.25 Visualise with acidic ammonium molybdate and UV $^1$H NMR Consistent with reference sample. $[\alpha]_D^{20}$=+88° (c=7, dichloromethane)

EXAMPLE 5

(—)-1,2-Bis-N-[2'-(diphenylphosphino)benzoyl]-1 (S), 2(S)-diaminocyclohexane 2-(Diphenylphosphino)benzoic acid (231.8 g, 0.756 mol, 2 eq) is suspended in dichloromethane (1700 ml) and cooled in an ice/water bath to 0° C. Triethylamine (122 ml, 0.87 mol) is added dropwise and a clear solution is obtained. This process is exothermic and a rise to 5° C. is observed. The solution is re-cooled to 0° C. and diphenylchlorophosphate (155.3 ml, 0.75 mol, 1.98 eq) is added slowly, maintaining the internal temperature between 0–5° C. The yellow solution is stirred for 1 hour at –5 to 0° C. During this time a precipitate is observed (NEt$_3$.HCl).

The (S,S)-1,2-diaminocyclohexane-D-tartrate salt (100 g, 0.378 mol, 1 eq) is suspended in water (600 ml) and potassium carbonate (172 g, 1.25 mol) is added. This process is exothermic and a clear solution is obtained after approximately 10 minutes.

After 30 minutes, the clear aqueous solution of diamine/ tartrate salt is added to the mixed anhydride at 0° C., and the resulting yellow two-phase mixture is stirred for 2 hours at 0° C., then allowed to warm to room temperature. After 14 hours, the mixture is poured into a 5 litre separating funnel. The organic phase is separated, washed with 2 N HCl (2×1000 ml) and saturated NaHCO$_3$ (soln) (2×1000 ml), then dried over magnesium sulphate. The dried organic phase is filtered through a silica pad and the pad is washed with dichloromethane (100 ml). The combined filtrates are evaporated to dryness under reduced pressure, producing a yellow/brown foam (261.4 g, 98% Th crude). The foam is crystallised from boiling acetonitrile (4.5 L) to afford a white crystalline solid. The solid is dried under vacuum to provide the title compound (180 g, 69% Th).

In an alternative recrystallisation procedure, the crude ligand (97 g) is dissolved in acetone (200 ml) and acetonitrile (1500 ml) is added; the mixture is heated to reflux to obtain complete solution, cooled to room temperature, filtered and washed with acetonitrile; and the white solid is dried under vacuum to provide the title compound.

(70 g, 72% recovery).

Mpt=134–136° C.

TLC (35% EtOAc/Hexanes) Rf=0.25 Visualise with acidic ammonium molybdate and UV $^1$NMR Consistent with reference sample. $[\alpha]_D^{20}$=–88° (c=7, dichloromethane).

We claim:

1. A process for the preparation of a compound having the formula

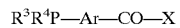

$R^3R^4P$—Ar—CO—X wherein Ar is an aryl group bearing the PR$^3$R$^4$ and COX groups in a 1,2-relationship, and optionally bearing also one or more non-interfering groups, R$^3$ and R$^4$ are each a hydrocarbon group optionally substituted by any non-interfering group, and X is an amine group, wherein said process comprises the reaction of R$^3$R$^4$P—Ar—COOY, OY being OH or a leaving group, with a solution of the amine obtained in situ by adding a base to a salt thereof.

2. The process, according to claim 1, wherein Ar is 1,2-phenylene.

3. The process, according to claim 1, wherein R$^3$ and R$^4$ are each phenyl.

4. The process, according to claim 1, for the preparation of a bidentate ligand of the formula

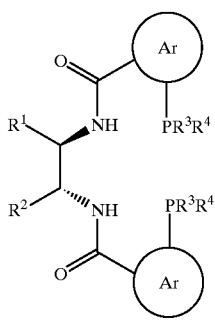

(3)

or the opposite enantiomer thereof, wherein $R^1$ and $R^2$ are each any non-interfering group, or $R^1$ and $R^2$ may be joined to form a ring, wherein said amine is a diamine of the formula

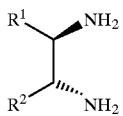

and OY is a leaving group.

5. The process, according to claim 4, wherein the diamine is either enantiomer of trans-1,2-diaminocyclohexane.

6. The process, according to claim 4, wherein the diamine is in the form of a salt with a chiral acid.

7. The process, according to claim 6, wherein the acid is tartaric acid.

8. The process, according to claim 4, which additionally comprises isolating the bidentate ligand as a crystalline solid, after recrystallisation from an organic solvent.

9. The process, according to claim 1, which is conducted in a biphasic aqueous/organic solvent mixture.

10. The process, according to claim 1, wherein Y is $-P(O)(OZ)_2$ and Z is a hydrocarbon substituent.

11. The process, according to claim 10, wherein is Z is phenyl.

12. The process according to claim 1, which additionally comprises the prior step of preparing the compound $R^3R^4P-Ar-COOH$ by reaction of $NaPR^3R^4$ with $F-Ar-COOH$ and, optionally, introducing a leaving group OY.

13. The process, according to claim 12, for the preparation of 2-(diphenylphosphino)benzoic acid, which comprises the reaction of 2-fluorobenzoic acid with $NaPPh_2$.

14. The process, according to claim 13, which comprises forming the $NaPPh_2$ from $PPh_2$, Na, and $NH_3$.

* * * * *